(12) United States Patent  
Mulligan (10) Patent No.: US 7,862,339 B2  
(45) Date of Patent: Jan. 4, 2011

(54) NEGATIVE WOUND PRESSURE THERAPY TEST SYSTEM

(75) Inventor: Sharon Mulligan, Bristol, RI (US)

(73) Assignee: Tyco Healthcare Group LP, Mansfield, MA (US)

( * ) Notice: Subject to any disclaimer, the term of this patent is extended or adjusted under 35 U.S.C. 154(b) by 151 days.

(21) Appl. No.: 11/901,767

(22) Filed: Sep. 19, 2007

(65) Prior Publication Data

US 2008/0077091 A1  Mar. 27, 2008

Related U.S. Application Data

(60) Provisional application No. 60/846,265, filed on Sep. 21, 2006.

(51) Int. Cl.  
G09B 23/28 (2006.01)

(52) U.S. Cl. ..................................................... 434/268

(58) Field of Classification Search ................. 604/543, 604/156; 434/267, 268  
See application file for complete search history.

(56) References Cited

U.S. PATENT DOCUMENTS 3,027,655 A * 4/1962 Alderson .................... 434/268  
4,661,093 A   4/1987 Beck et al.

2002/0143286 A1   10/2002 Tumey  
2002/0198503 A1   12/2002 Risk, Jr. et al.  
2002/0198504 A1 * 12/2002 Risk et al. .................. 604/318

FOREIGN PATENT DOCUMENTS

WO   WO 2006046060   5/2006

OTHER PUBLICATIONS

Great Britain Search Report, Application No. GB 0718399.9, dated Dec. 3, 2007.

* cited by examiner

*Primary Examiner*—Nicholas D Lucchesi  
*Assistant Examiner*—Pritesh Patel  
(74) *Attorney, Agent, or Firm*—Elizabeth A. O'Brien, Esq.

(57) ABSTRACT

A system for testing a negative pressure wound dressing, includes a simulated wound having a housing and a wound cavity within the housing, and having a shape and dimension representative of an actual wound type, a wound dressing positionable at least over the simulated wound, a negative pressure source in fluid communication with the wound cavity, at least one sensor adapted to record at least one parameter within the simulated wound, an air leak model including a valve in fluid communication with the wound cavity whereby opening of the valve simulates an air leak within the wound cavity, a fluid source in fluid communication with the wound cavity for delivering fluid to the wound cavity to simulate presence of exudates and a computer coupled to the at least one sensor for recording and analyzing data recorded by the at least one sensor to thereby providing an indication of functioning of the system.

16 Claims, 10 Drawing Sheets

NEGATIVE WOUND PRESSURE THERAPY TEST SYSTEM

CROSS REFERENCE TO RELATED APPLICATION

The present application claims priority to, and the benefit of, U.S. Provisional Application Ser. No. 60/846,265, filed Sep. 21, 2006.

BACKGROUND

1. Technical Field

The present disclosure relates to treating an open wound with negative wound pressure, and, more specifically, relates to a testing system which analyzes the effectiveness of a negative wound pressure therapy apparatus.

2. Description of Related Art

Wound closure involves the migration of epithelial and subcutaneous tissue adjacent the wound towards the center of the wound until the wound closes. Unfortunately, closure is difficult with large wounds or wounds that have become infected. In such wounds, a zone of stasis (i.e. an area in which localized swelling of tissue restricts the flow of blood to the tissues) forms near the surface of the wound. Without sufficient blood flow, the epithelial and subcutaneous tissues surrounding the wound not only receive diminished oxygen and nutrients, but, are also less able to successfully fight microbial infection and, thus, are less able to close the wound naturally. Such wounds have presented difficulties to medical personnel for many years.

Wound dressings have been used in the medical industry to protect and/or facilitate healing of open wounds. One technique has been to use negative pressure therapy, which is also known as suction or vacuum therapy. A variety of negative pressure devices have been developed to allow excess wound fluids, i.e., exudates to be removed while at the same time isolating the wound to provide protection and, consequently, shorten recovery time. Various wound dressings have been modified to promote the healing of open wounds.

Issues that continually need to be addressed when using a wound dressing in negative pressure therapy include ease of use, efficiency of healing a wound, and sufficient drainage of wound exudates. Thus, there remains a need to constantly improve negative pressure wound dressings for open wounds.

SUMMARY

Accordingly, the present disclosure is directed to a testing system for checking the effectiveness of a negative wound pressure therapy (NWPT) apparatus. The testing system includes a simulation wound apparatus and a computing apparatus. The simulation wound apparatus includes a simulated wound fixture and an exudates bath. The simulated wound fixture may be representative of a wound-type encountered in a clinical setting. A negative pressure conduit is in fluid communication with the wound fixture. The simulation wound apparatus may include at least two testing simulations: e.g., incorporating a peristaltic pump for 1) simulating liquid flow from the exudates bath into the wound, and a valve/flow meter for 2) simulating air leaks within the wound dressing. The testing system also may include a plurality of wound sensors adapted for measuring temperature, pressure, oxygen, RH %, light etc. within the wound as well as pressure sensors, flowmeters, etc. The sensors are connected to the computing apparatus and are adapted to provide the measured data via corresponding voltage signals thereto. The computing apparatus includes a user interface for controlling the simulation wound apparatus and recording the data provided by the sensors. The wound dressing therapy apparatus to be tested may include a wound dressing and a negative pressure source. The wound dressing is positioned with respect to the wound fixture. The negative pressure pump is connected to the negative pressure conduit.

According to one aspect of the present disclosure, a system for testing a negative wound pressure therapy apparatus is provided. The system includes a simulated wound having a housing and a wound cavity disposed within the housing. The wound cavity has a shape and dimension representative of an actual wound type. An exudates model including an exudates bath and a pump is in communication with the wound cavity. The exudates bath stores at least one of a fluid and exudates. The pump is adapted to deliver at least one of the fluid and the exudates into the simulated wound. The system further includes at least one sensor adapted to record at least one testing property of the simulated wound. An air leak model having a valve connected to the simulated wound also may be provided. Opening of the valve simulates an air leak or can be used to deliver oxygen at a controlled rate. A computing apparatus is coupled to the at least one sensor, the negative pressure source, the air leak model and/or the exudates model to record and analyze data from the simulated wound. The negative wound pressure therapy apparatus to be tested includes a wound dressing which is positioned to cover the wound cavity and a negative pressure pump. The negative pressure pump is activated to create a vacuum condition within the wound cavity.

BRIEF DESCRIPTION OF THE DRAWINGS

Various embodiments of the testing system of the present disclosure are described herein with reference to the drawings wherein.

DESCRIPTION OF THE PREFERRED EMBODIMENT(S)

In general, the present disclosure is directed to a testing system for testing the effectiveness of a negative pressure wound therapy apparatus. The testing system includes a simulated wound and a computer incorporating a plurality of sensors. The testing system collects data and transmits the data to a computing apparatus wherein the data is processed and analyzed.

Figure 1:
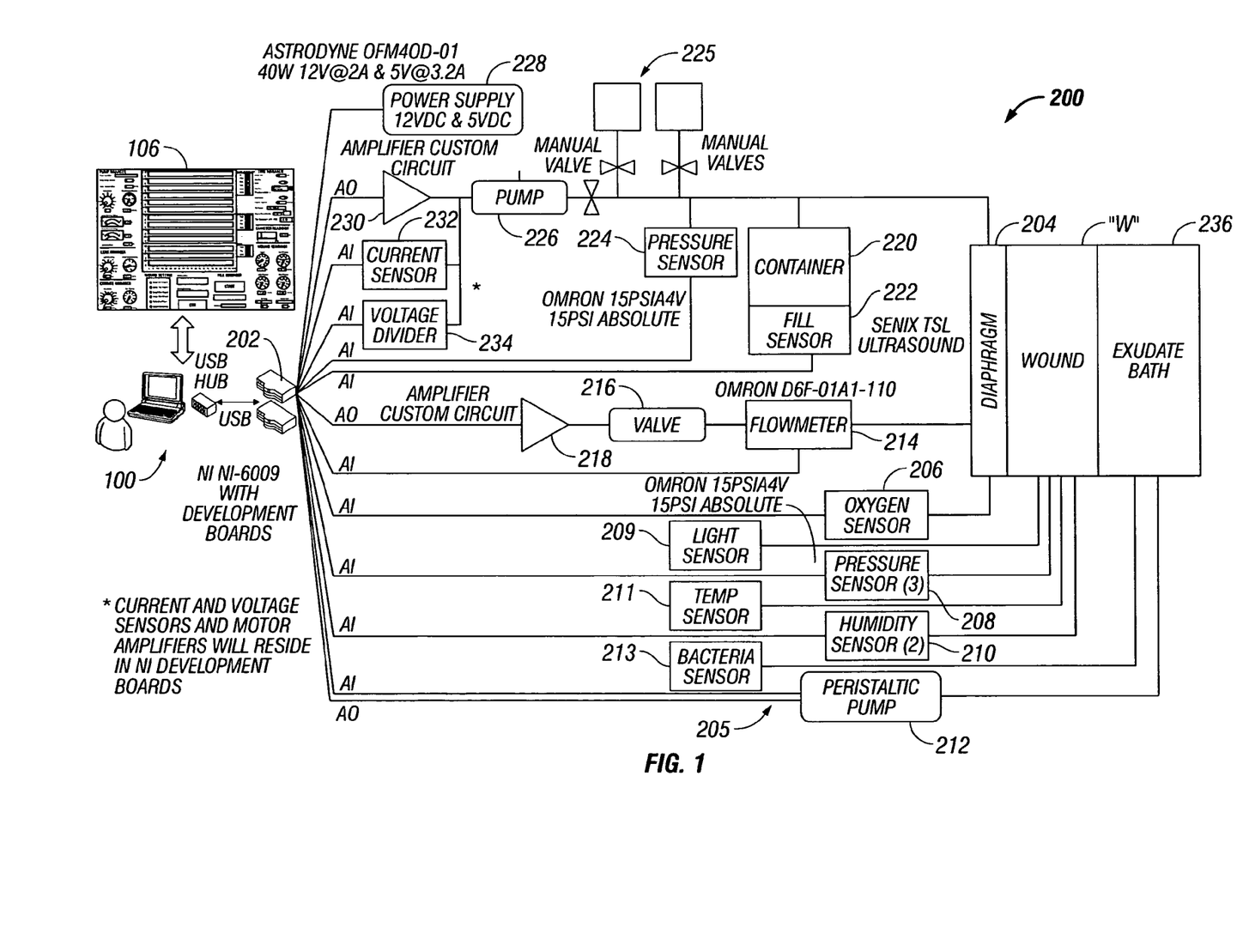
FIG. 1 is a schematic view of a testing system of the present disclosure illustrating the simulated wound apparatus and a computing apparatus.

Referring now to FIG. 1, the testing system 10 for testing the effectiveness of the negative pressure wound therapy apparatus in accordance with the principles of the present disclosure is illustrated. The negative wound therapy apparatus will, at a most basic level, include a wound dressing 204 and a negative pressure source 226. The wound dressing 204 is adapted to operate with simulated wounds such as wound "w."

The wound dressing 204 can be any conventional wound dressing adapted for applying negative pressure. One wound dressing suitable for use is disclosed in commonly assigned U.S. Provisional Patent Appln. Ser. No. 60/765,921 filed Feb. 7, 2006 and depicted in FIG. 3. Wound dressing 204 may includes several components, namely, at least a support layer or member 204a which is contact with the wound "w", an outer layer or cover member 204b and a plurality of beads 204c supported by the support member 204a. The support member 204a is adapted to substantially conform to the topography of the wound "w." The support member 204a may be substantially porous to permit exudates to pass from the wound "w" through the support member 204a. Support member 204a may also be non-adherent. The support member 204a may be constructed from a variety of different materials. These materials may include but are not limited to synthetic non-absorbable polymer fibers such as carbonized polymers, polyethylene (PET), polypropylene (PP), polytetrafluoroethylene (PTFE), Nylon, arimids, Kevlar, polyethylene terephthalate (PET) or natural fibers such as cellulose.

Figure 3:
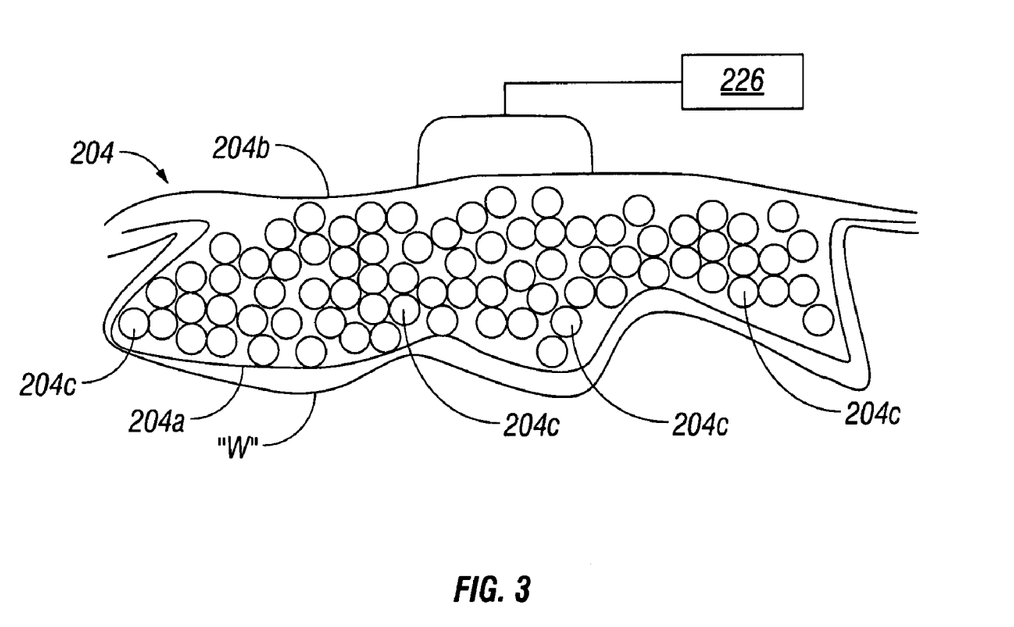
FIG. 3 is an embodiment of an exemplative wound dressing to be tested and mounted to the simulated wound apparatus.

The outer member 204b of the wound dressing 204 encompasses the perimeter to surround and form a seal around the wound "w". For instance, the sealing mechanism may be any adhesive bonded to a layer that surrounds the wound "w." Adhesives include, for example, medical grade acrylics like the adhesive used with CURAFOAM ISLAND™ dressing of TycoHealthcare Group, LP or any silicone or rubber based medical adhesives that are skin friendly and non irritating. The outer member 204b may be provided with an adhesive backing and/or alternatively, an adhesive may be applied to the outer member 204b during the procedure.

The outer member 204b is typically a flexible material, e.g., resilient or elastomeric, that seals the top of wound dressing 204. Exemplary flexible materials include the transparent dressing manufactured under the trademark Polyskin II by Kendall Corp, a division of Tyco Healthcare Group LP. Preferably, the outer member 204b is transparent and provides a barrier to microbes and fluid containment. The outer member 204b may be manufactured from a semi-permeable plastic film providing it with a high moisture vapor transmission rate (MVTR) to allow the passage of moisture through the film. Such films could be manufactured from polyurethanes, breathable polyolefins, or copolyesters. The transparency of the outer member 204b permits a visual review of the status of the wound dressing. Alternatively, the outer member 204b may be impermeable to moisture vapors.

The beads 204c are manufactured from a suitable biocompatible material. The beads 204c may be antimicrobial beads, beads with growth factors, medicaments, antibiotics, analgesics, and healing factors such as vitamins, nutrients and the like. These beads 204c may be non-adherent and may be bioabsorbable over a predetermined period of time. Acrylic (PMMA) can be used for its clarity. Other materials that could be used are polycarbonate, polystyrene, PVC, ABS, SAN, glass or silicone. Bioabsorbable polymers could also be used, e.g., polylactide (PLA), polyglycolide (PGA), Chitosan, polyethylene oxide (PEO) or polyethylene glycol (PEG).

The beads 204c are preferably substantially rigid for at least a predetermined period of time during healing so as to maintain the desired spacing to thereby define passages through the bed of beads for passing of wound exudates, air, etc. Thus, the beads 204c may be nonabsorbable. Alternatively, the beads 204c and bead size may be partially or fully absorbable. With an absorbable material, the rate of absorption of the beads 204c is selected to maintain the desired rigidity during a predetermined period of healing.

Alternatively, the beads 204c may be substituted with an absorbable dressing manufactured under the trademark Kerlix™ by Kendall Corp, a division of Tyco Healthcare Group LP.

The negative pressure source 226 to be tested applies vacuum through conduit to the wound "w." The negative pressure source 226 may be an automated pump. Typically, the negative pressure generated within the wound "w" by negative pressure source 226 is in a range between about 20 mmHg to about 500 mmHg, more preferably, about 75 mmHg and about 125 mmHg. The portable pump may be in the form of a small or miniature pump that maintains or draws adequate and therapeutic vacuum levels. The pump may be a peristaltic pump or a continuous pump. Typically, negative pressure source 226 has regulation means to apply the optimal vacuum pressure for healing the wound.

Referring again to FIG. 1, the testing system 10 will be discussed. The testing system 10 includes simulation wound apparatus 200 and computing apparatus 100 which collects data from the simulation wound apparatus 200. The testing system 10 further includes an exudates model having an exudates bath 236 connected to the simulated wound "w" (e.g., in fluid communication with the simulated wound "w"). The exudates bath supplies exudates and fluid to the wound "w" for the simulation of exudates and fluid flow into the wound "w." The testing system 10 also includes an air leak model which simulates flow of air within the dressing apparatus 200. The simulated wounds may be created in a laboratory setting.

Figure 2A:
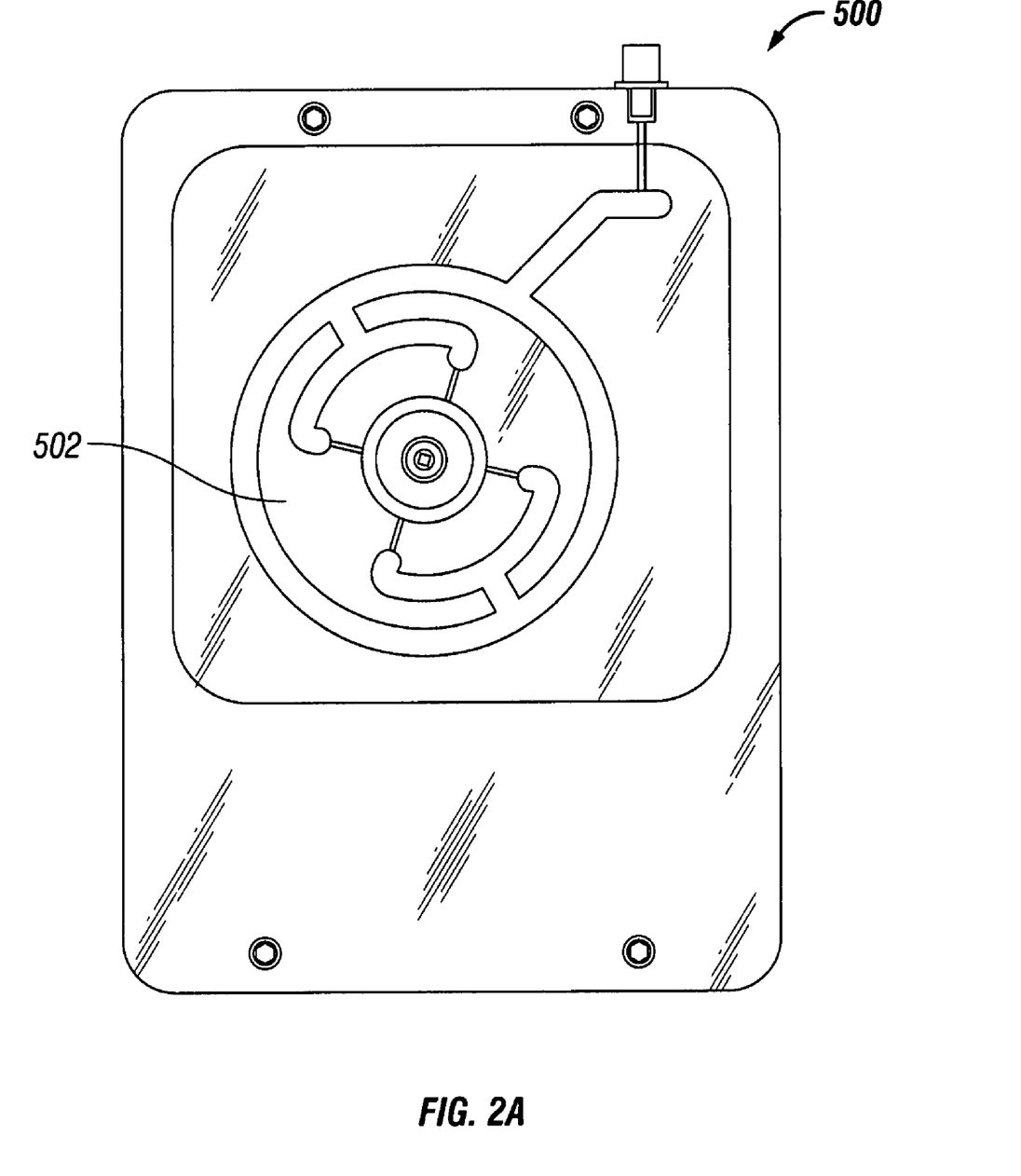
FIGS. 2A-2E are perspective views of simulated wounds apparatti according to the present disclosure.
Figure 2B:
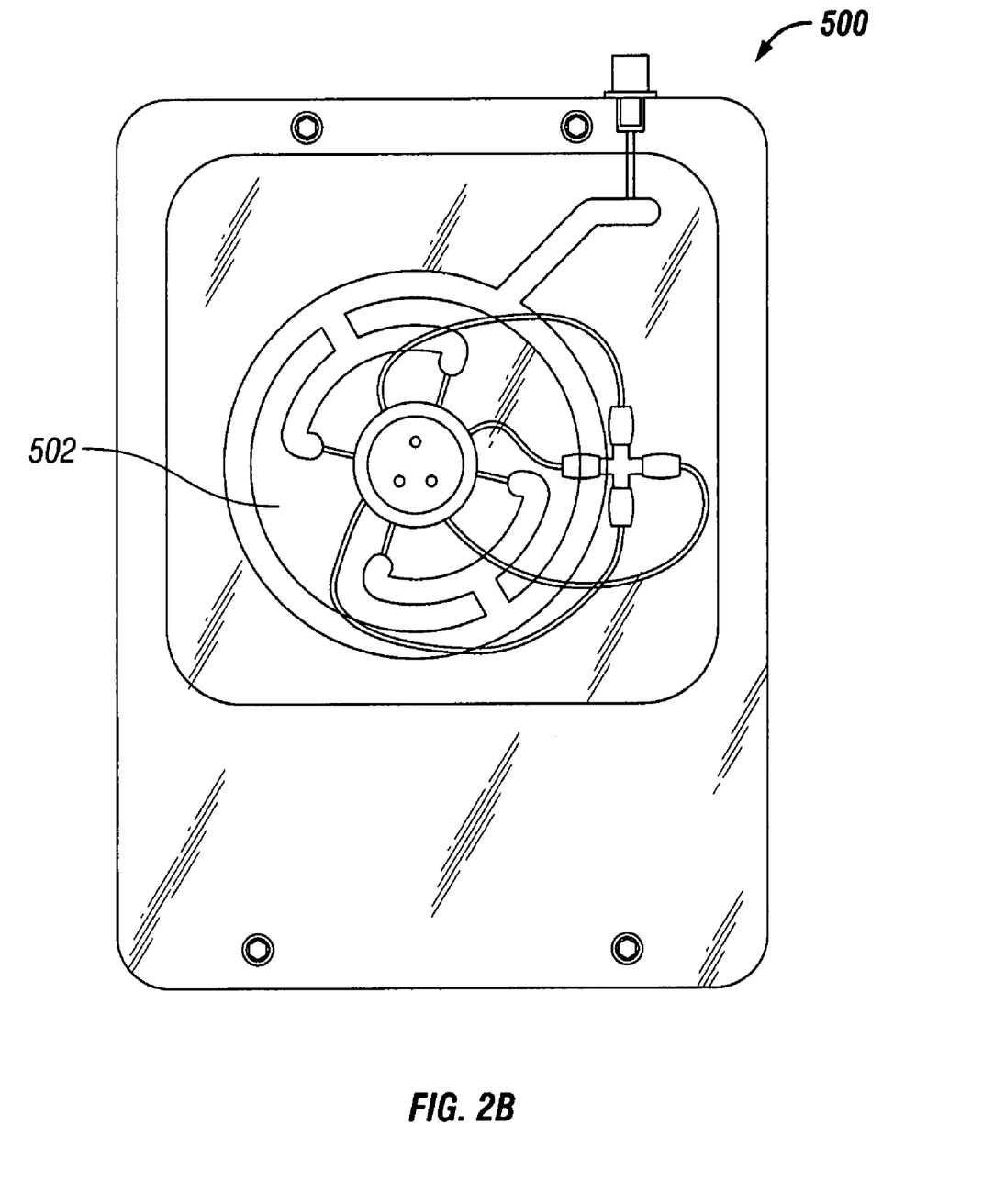
Figure 2C:
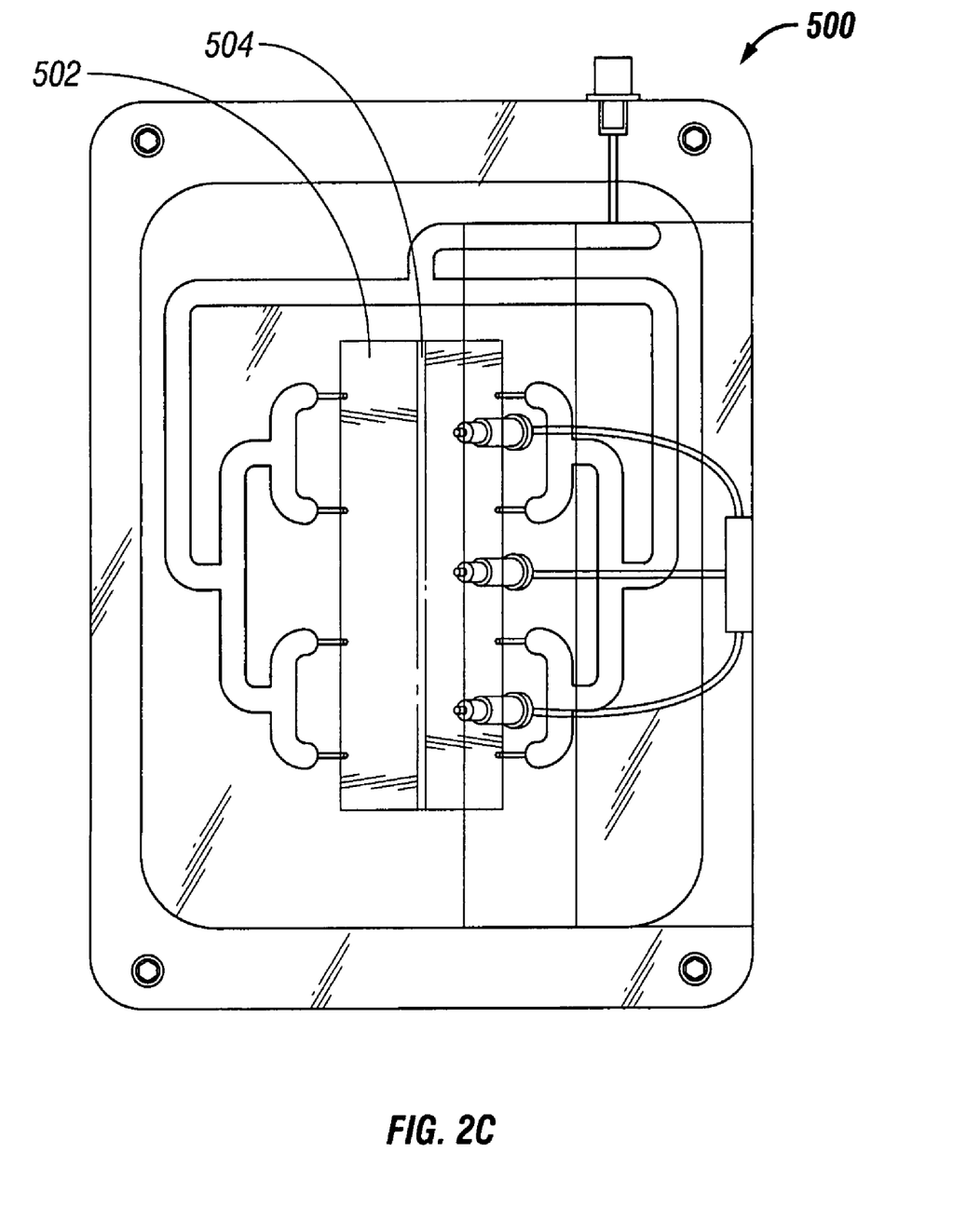
Figure 2D:
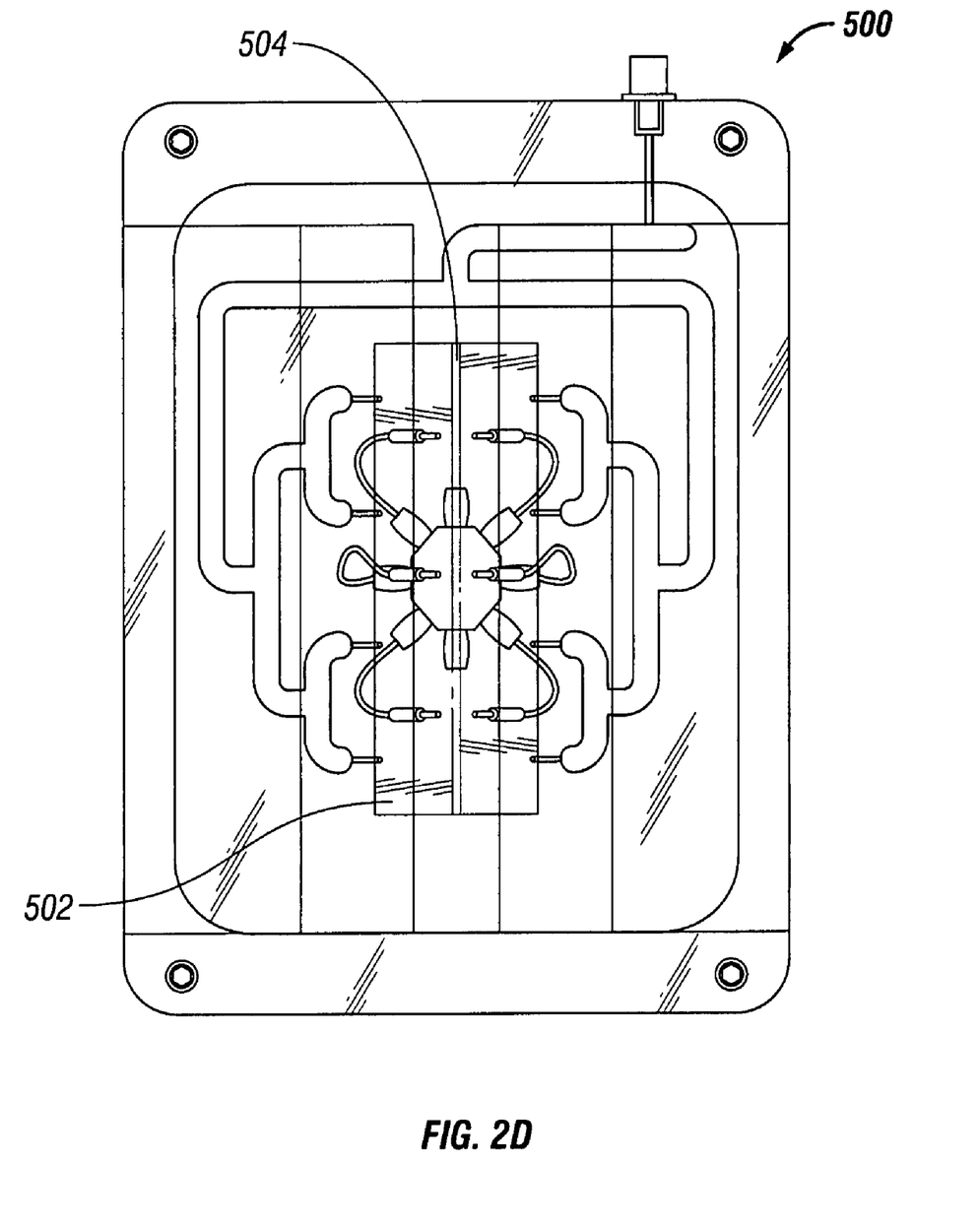
Figure 2E:
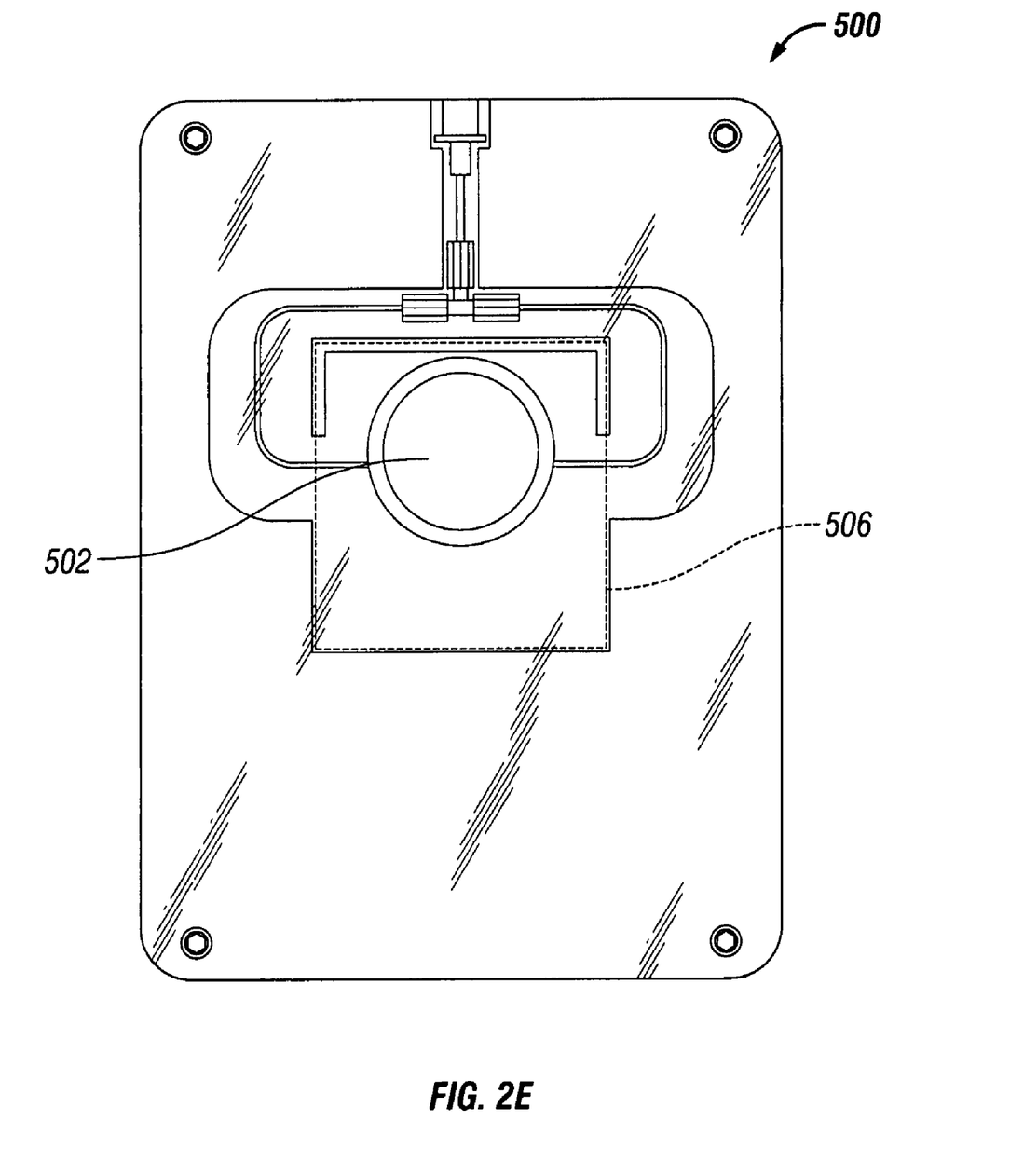

FIGS. 2A-2E illustrates embodiments of various simulated wounds "w" which are representative of wound-types encountered in a clinical setting. Simulated wound "w" includes a housing or fixture 500 having a wound cavity 502 disposed within the housing 500. The housing 500 may be constructed from a variety of materials such as Lucite™ polycarbonate, metals, plastics etc. capable of withstanding pressure changes occurring during the testing process. The wound cavity 502 may be of various shapes and dimensions representative of various types of wounds encountered by a clinician, including, e.g., a small dry wound (FIG. 2A), small wet wound (FIG. 2B), large dry wound (FIG. 2C), large wet wound (FIG. 2D) and tunneling wound (FIG. 2E). For exemplative purposes, the small dry and wet simulated wounds of FIGS. 2A and 2B may have wound cavities 502 occupying a volume of 7.5 cubic centimeters (cc) defining a diameter of 40 millimeters (mm) and a depth of 6 mm. The large dry and wet simulated wounds of FIGS. 2C and 2D may have wound cavities 502 which are V-shaped and occupy a volume of 480 (cc). The dimensions of the V-shaped wound cavity 502 may be 160 (mm) in length, 80 (mm) in width and 75 (mm) in depth at the vertex 504 of the V-shaped cavity 502. The tunneling wound of FIG. 2E may have a wound cavity 502 which occupies a volume 55 (cc). The tunneling wound may have an initial diameter of 65 (mm) and a total depth of 95 (mm). The tunneling section 506 (shown in phantom) of the wound cavity 502 may begin at 40 (mm) in depth and extend for a length of 105 (mm). The wet and dry characteristics may be controlled by fluid or exudate(s) flow from the exudate(s) bath. Other wound types are also contemplated. The wound cavity 502 may be constructed from a variety of materials similar to the materials used to manufacture the housing 500, but may be designed to either remain rigid under pressure or collapse to simulate flexibility of human tissue in clinical setting.

In use, the wound dressing 204 is placed on the simulated wound "w" as shown in FIG. 1. The negative pressure source 226 is then activated creating a reduced pressure state within wound dressing 204. As the pumping progresses, wound exudates flow through support member and the out conduit. Preferably, the wound exudates are deposited within a container 220 coupled in line with the conduit and negative pressure source 226.

The container 220 collects the exudates and is connected to a fill sensor 222 which detects the amount of exudates within the container 220. The negative pressure source 226 is powered by a power supply 228 which is preferably a low voltage DC power source (e.g., a battery). The negative pressure source 226 is controlled via circuitry 230 (e.g., pressure regulator which controls the pressure set point, power, etc.). Furthermore a current sensor 230 and a voltage divider 234 monitor the actual voltage and current being supplied at the terminals of the negative pressure source 226. The conduit connecting the wound dressing 204 to the negative pressure source 226 includes a manual and/or automatic control valve which allows a user to disconnect the pump. Additional negative pressure sources 225, each having individual control valves, may be interchangeably connected to the conduit to perform various tests and evaluate efficiency of various pumps. It is envisioned that the negative pressure source 226 may be disconnected and one of the negative pressure sources 225 are connected to the conduit. A pressure sensor 224 is also connected to the conduit between the negative pressure source 226 and the wound dressing 204 to record the pressure.

The fill sensor 222, the pressure sensor 224, the circuitry 230, the current sensor 232, the voltage divider 234, and the power supply 228 are connected to a computer interface 202 which is connected to the computing apparatus 100 through a communication port 102. This allows for recordation of data collected by the fill sensor 222, the pressure sensor 224, the current sensor 232 and the voltage divider 234. The computing apparatus 100 is also adapted to control the circuitry 230 and the power supply 228 thereby controlling the operation of the negative pressure source 226.

Figure 4:
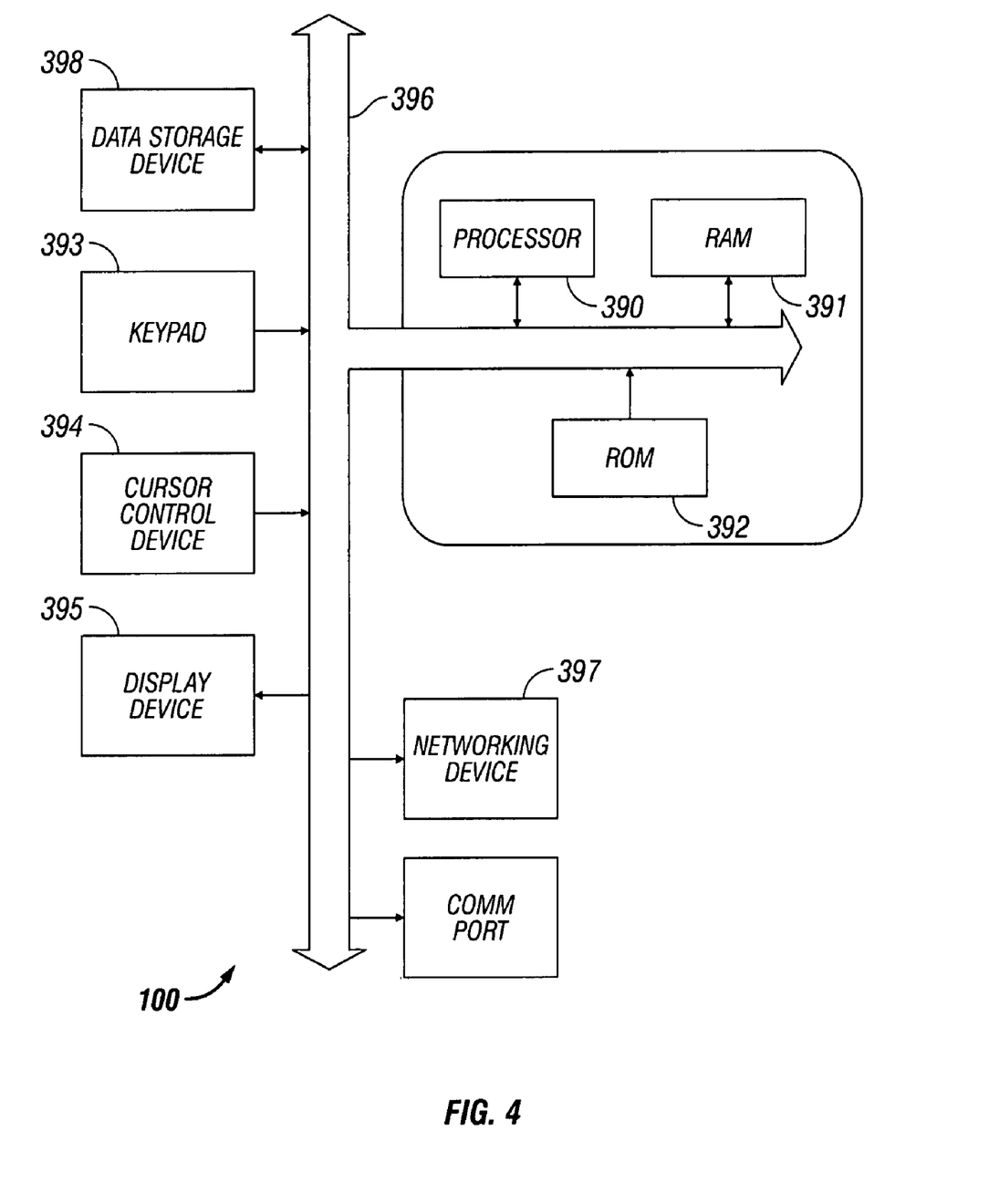
FIG. 4 is a schematic diagram of the computing apparatus.

With reference to FIG. 4, the computing apparatus 100 may include one or more central processing units (CPU) 390, a random access memory (RAM) 391, a read only memory (ROM) 392 and input/output (I/O) interface(s) such as a keypad 393, cursor control device 394 (e.g., a mouse, joystick, touchscreen, etc.), a data storage device 398, and display device 395. The computing apparatus 100 also includes a networking device 397 which provides wired or wireless connectivity to a communications network. In addition, various other peripheral devices may be connected to the computing apparatus 100 by various interfaces and bus structures, such as the communication port 102 (e.g., a parallel port, serial port or universal serial bus (USB), etc.). A system bus 396 couples the various components and may be any of several types of bus structures including a memory bus or memory controller, a peripheral bus, and a local bus using any of a variety of bus architectures.

The computing apparatus also includes an operating system and/or micro instruction code. The various processes and functions described herein may either be part of the micro instruction code, firmware, or part of the application program (or a combination thereof) which is executed via the operating system. In addition, the computing apparatus 100 includes software for displaying user input screens and recording user responses, which is discussed below. More specifically, the computing apparatus 100 includes a user interface 106 adapted to control various components of the wound dressing apparatus 200.

It is to be further understood that because some of the constituent system components and method steps depicted in the accompanying figures may be implemented in software, the actual connections between the system components (or the process steps) may differ depending upon the manner in which the present disclosure is programmed. Given the teachings of the present disclosure provided herein, one of ordinary skill in the related art will be able to contemplate these and similar implementations or configurations of the present disclosure.

With reference to FIG. 1, a plurality of wound sensors 205: an oxygen sensor 206, a pressure sensor 208, a light sensor 209, a humidity sensor 210, a temperature sensor 211, and a bacterial level indicator 213 are disposed at the wound "w." The wound sensors 205 provide data on the wound "w" as the wound is subjected to negative pressure treatment. This allows for evaluation of efficacy of various treatments (e.g., determining optimal pump pressure and wound dressing for particular wounds). The oxygen sensor 206 detects the level of oxygen at the wound; the pressure sensor 208 is coupled to the conduit connecting the negative pressure source 226 and the container 220, the pressure sensor 208 detects the negative pressure at the wound achieved via the action of the negative pressure source 226; the light sensor 209 measures amount of UV and/or IR light at the wound "w" which is helpful in analyzing permittivity of the wound dressing 204; the humidity sensor 210 detects the amount of water (vapor or liquid) at the wound "w" which is helpful in analyzing efficiency of the negative pressure source 226 and the wound dressing 204 at withdrawing moisture from the wound "w"; the temperature sensor 211 detects the temperature at the wound "w"; the bacterial level indicator 213 detects various types of bacteria and amounts thereof present at the wound "w." The wound sensors 205 are also connected to the computing apparatus 100 through the computer interface 202. It is envisioned that multiple sensors of one type may be used, e.g., two pressure sensors, depending on the size of the wound being monitored.

The simulation wound apparatus 200 also includes a valve 216 which is connected to the wound dressing 204 or the simulated wound "w" through another conduit. The valve 216 controls air flow of simulated air leaks into the wound, such that when the valve 216 is open air may flow into the simulated wound "w." The valve 216 is controlled automatically through a valve control circuit 218 to maintain a preset user selected flow rate. A feedback control loop is implemented to maintain user selected flow rate, wherein the flowmeter 214 measures the flow rate and provides sensed feedback information to the control circuit 218 which then makes adjustments to the flow rate in response thereto. The flowmeter 214, the wound sensors 205, the pressure sensor 224, the fill sensor 22, the current sensor 232, the voltage divider 234, and the power supply 228 convert the measured data into corresponding voltage signals which are then transmitted to the computing apparatus 100.

A peristaltic pump 212 is connected to the exudates bath 236 to maintain pressure therein to provide desired pressure conditions for simulation purposes (e.g., increase or decrease the flow of exudates and fluid into the wound "w"). Typical peristaltic pumps include a plurality of rollers that are driven along in a circular path by an electric motor (or other suitable prime mover) in a rotational direction. As is common in most such peristaltic pumps, rollers periodically contact and compress the tubing and as the rollers move along the circular path, successive pockets of air are suctioned through the tubing. The peristaltic pump 212 is controlled by the computing apparatus 100 (e.g., set point) and reports the pressure, pump velocity and velocity feedback provided thereby via tachometer. Hence, the user controls the peristaltic pump 212 to adjust and monitor the flow of liquid into the wound model. It is envisioned that the peristaltic pump 212 may be replaced by any automatic pump.

Figure 5:
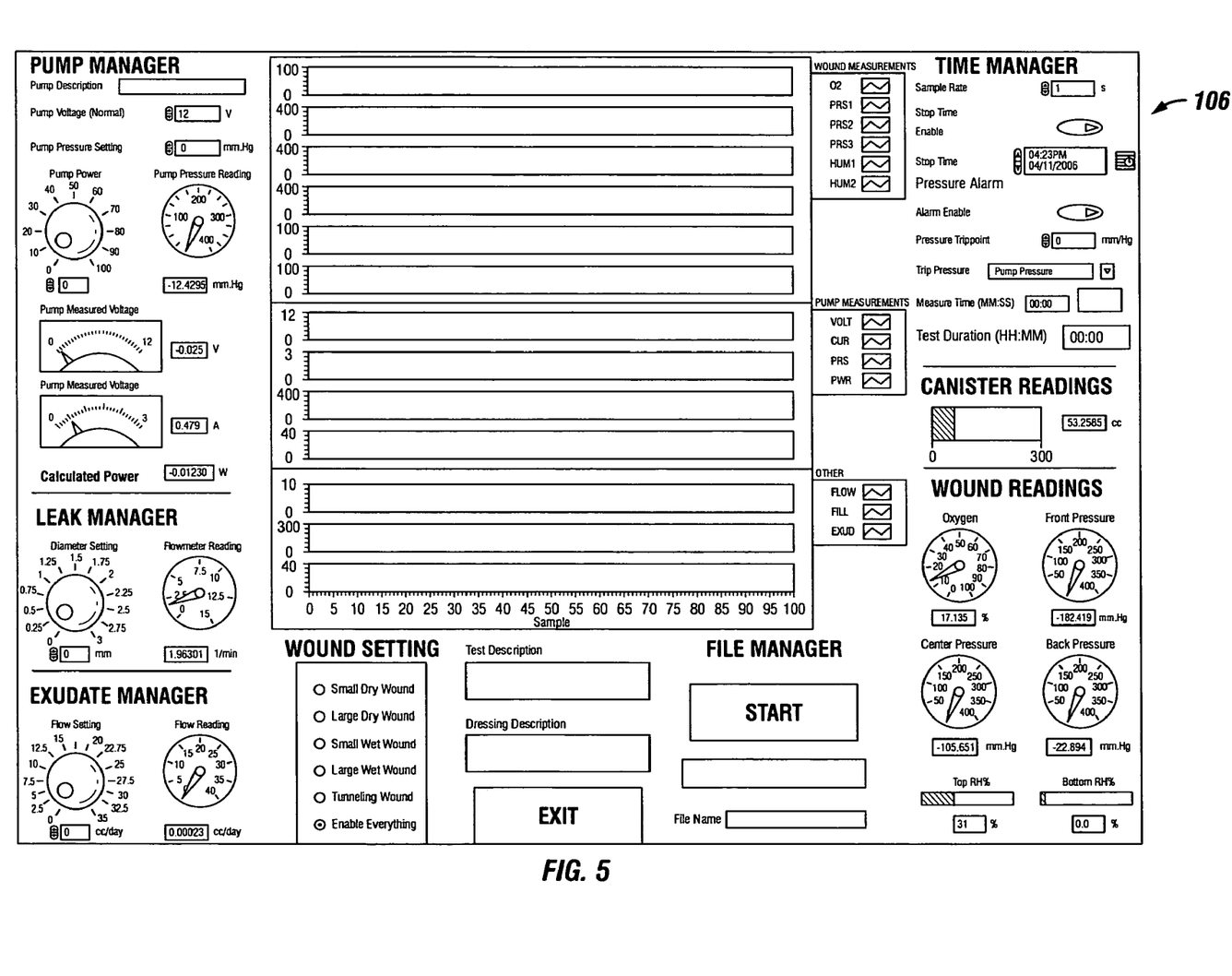
FIG. 5 is a schematic diagram of a user interface according to the present disclosure.

With reference to FIG. 5, the user interface 106 is shown. The user interface 106 displays on the display device 395 data recorded by the sensors and allows the user to adjust various testing parameters, such as a set point for the negative pressure source 226. The computing apparatus 100 records the data recorded by the wound sensors 205 and the flowmeter 214 and controls the valve 216, the negative pressure source 226 and the peristaltic pump 212 via the user interface 106. It is envisioned that the sensor feedback information may be stored in a separate file accessible at a later time. The user interface may be application software written for LabVIEW (Laboratory Virtual Instrumentation Engineering Workbench), which is a platform and development environment. In particular, the user interface 106 controls input voltage of the negative pressure source 226, monitors and records actual voltage and current used, sets and controls air flow of leaks into the wounds (i.e., via the vale 216), sets and records the flow of fluid into the wounds and measures fill level of fluid in the container 220. The testing system 10 allows for evaluation of various pumps (e.g., interchangeable negative pressure source 226), evaluation of multiple wound dressing technologies, instrumentation of multiple wound models and calculation of power consumption.

The user interface 106 provides the user with ability to enter pump information (e.g., negative pressure source 226) which may include pump description. The user also sets pump operating parameters, such as, nominal pump voltage, pump pressure setting (entered either in mmHg or in Hg), pump power which is voltage level applied to the pump, wherein 100% is equivalent to nominal voltage. The user interface 106 also outputs the following pump parameters: pump pressure reading which is read by the pressure sensor 208 (either in mmHg or in Hg), pump measured voltage which is measured at the terminals of the pump by the voltage divider 234, pump measured current also measured at the terminal of the pump by the current sensor 232, and calculated power obtained by multiplying measured voltage and current.

The user interface 106 also includes a leak manager which allows the user to set diameter of the opening of the valve 216. The diameter value sends a corresponding voltage command to the valve control circuit 218 which then opens the valve 216 to the desired setting. The leak manager also reports the reading by the flow meter 214 which measures the air flow in the leak model in liters per minute.

It is also contemplated that the user interface 106 includes an exudates manager which allows the user to set the flow setting which controls the revolutions of the peristaltic pump 212 and, hence, the flow of exudates from the exudates bath 236. The exudates manager also reports the reading from the tachometer output of the peristaltic pump 212. The user also selects an appropriate wound model using the interface 106 as discussed in more detail below.

The user interface also includes a system information section which includes a test description field, a dressing description field for inputting information regarding the dressing being tested, status display which indicates whether sensor data is being recorded by displaying "IDLE" or "RECORDING" accordingly. A "START" button is shown which initiates tests, starts or stops data logging of all the sensors and resets timers. An "EXIT" button is provided for terminating the program. A file name field allows the user to select a file for storing the sensor data being recorded once the "START" button is pressed.

The time manager includes a sample rate field which displays the sampling rate (e.g., in seconds) at which sensors collect data, a stop time enable field which accepts an input of a predetermined time period at which to terminate the test, a stop time button for stopping the test. The time manager also includes a pressure set point field for inputting a predetermined set point during the test and a pressure alarm enable button which enables monitoring and capture of the time period for reaching the pressure set point, the captured value is then displayed in the measured time field. The time manager also includes a test duration field which displays duration of the test.

The user interface 106 further includes a wound readings section which displays data from the wound sensors 205 and a plotting area. The plotting area is subdivided into three sections wherein the first section plots the data collected by the wound sensors 205 (e.g., one plot per sensor) vs. time, the second section plots the data (e.g., voltage, current, pressure and power) collected by pump sensors (e.g., current sensor 232, voltage divider 234, and pressure sensor 224), and the third section plots the data collected by the flow meter 214, the fill sensor 222 and the tachometer of the peristaltic pump 212.

With regard to simulation of multiple wound models, during operation the user selects one of a plurality of available wound models. In response to selecting a particular wound model, the user interface 106 automatically selects certain wound sensors 205 to monitor the wound "w." In particular, certain types of wounds only require certain types of sensor whereas other types of wound models require other types of sensors simply because not all sensor data is relevant to all wound models.

Figure 6:
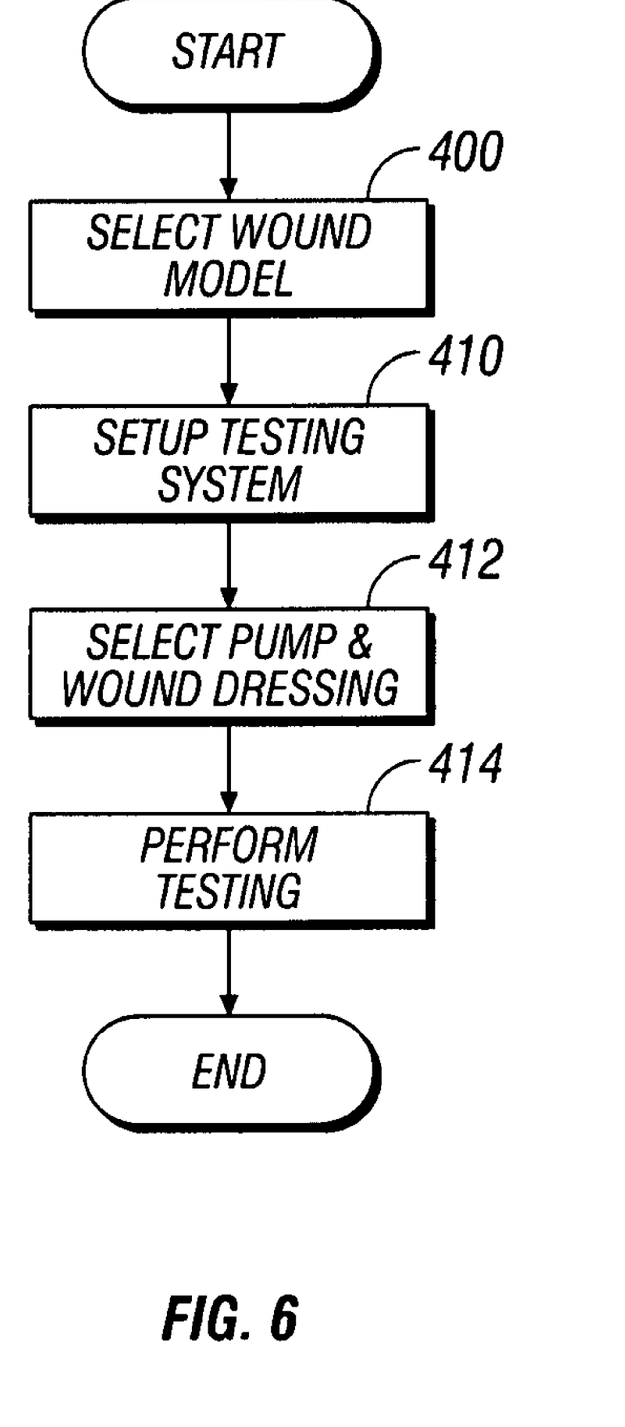
FIG. 6 is a flow diagram of a procedure performed by the testing system

A wound testing method is illustrated in FIG. 6. Initially, using the user interface 106 a wound model is selected in step 400. A wound model is described as having three characteristics: size—either small or large, moisture content—either wet or dry, and structure either compliant or rigid. Thus making for the total of five different wound models: small rigid dry wound (e.g., chronic leg ulcer), large rigid dry wound (e.g., acute wound), small rigid wet wound, large rigid wet wound, compliant wound (e.g., collapsible and/or tunneling wound).

In step 410, the user interface 106 automatically configures the testing system 200. The user interface 106 selects which of the wound sensors 205 are to be used during the test based on the wound model selected as well as other equipment which has to be turned on. For rigid dry wounds, at least pressure sensor 208 and oxygen sensor 206 are selected. For large dry rigid wounds, two pressure sensors 208 are used. For rigid wet wounds at least one humidity sensor 210 and at least one pressure sensor 208 are selected. At least two pressure sensors 208 are activated if the wound is large. Further, for wet wounds pumping of the fluid into the wound "w" is achieved via activation of the pump 212. For collapsible wounds, at least three pressure sensors 208 and at least one humidity sensor 206 are activated. The user may select additional sensors which were not automatically activated by the user interface 106, e.g., light sensor 209, temperature sensor 211.

In step 412, the user selects a pump as the negative pressure source 226 and the type of the wound dressing 204. It is envisioned that the user enters description of the pump and the wound dressing being used in the test.

In step 414, the user begins the application wherein the negative pressure source 226 is activated and as the negative pressure is created within the wound dressing 204, the wound sensors 205 record collected data. The user sets the time period for the test and adjusts the sampling rate for the sensors. The user also sets up the simulated air leak by adjusting the valve 216 and the simulated flow of liquid into the wound "w" via the peristaltic pump 212. Further, the user calibrates the sensors if required.

The user initiates recordation of data and may be prompted by the user interface 106 where to save the data. The user can set a specified pressure set point, if achieved may be signaled via an audio and/or visual alarm (not explicitly shown). The user interface 106 displays graphically and/or in a text line pump pressure, wound pressure, oxygen, humidity, volumetric fill, air leak rate, fluid flow, pump power consumption by measuring current consumption and applied voltage, measured pump voltage, measured pump current, air leak setting, measure leak rate, time elapsed, etc. These values may be displayed vs. time in a graph. Further, set values and measured values may be displayed along side each other for easier comparison of the test results. The test is terminated when the time set by the user is expired or the test is manually stopped.

The collected data this provides a quantitative measurement of the effectiveness of the negative wound pressure treatment apparatus including wound dressing type and negative pressure source for a predetermined wound type. This data may be interpreted to adjust various parameters, materials, etc. of the proposed testing system in a manner to ensure the overall effectiveness of the system and/or to achieve other wound parameters. Moreover, the testing system may be utilized to provide a standardized methodology for establishing accepted industry standards in negative wound pressure treatment. During testing, the RH may be in the range from about 0% to about 100%, wound pressure may be from about 0 mmHg to about 500 mmHg and oxygen level may be from about 0% to about 100%.

While the disclosure has been illustrated and described, it is not intended to be limited to the details shown, since various modifications and substitutions can be made without departing in any way from the spirit of the present disclosure. As such, further modifications and equivalents of the invention herein disclosed can occur to persons skilled in the art using no more than routine experimentation, and all such modifications and equivalents are believed to be within the spirit and scope of the disclosure as defined by the following claims.

What is claimed is:

1. A testing system for testing a negative pressure wound therapy apparatus of the type including a wound dressing adapted for positioning over a wound and a negative pressure source, the testing system comprising:
   a simulated wound having a housing and a wound cavity within the housing, the wound cavity having a shape and dimension representative of an actual wound type, and adapted to accommodate the wound dressing of the negative pressure wound therapy apparatus positioned there over;
   a negative pressure conduit in fluid communication with the wound cavity and connectable to the negative pressure source of the negative pressure wound therapy apparatus;
   at least one sensor adapted to record at least one parameter within the simulated wound;
   an air leak model having a valve in fluid communication with the wound cavity, the valve being controllable to introduce atmospheric air to simulate an air leak within the wound cavity; and
   an exudates model having an exudates bath disposed in fluid communication with the simulated wound.

2. The testing system according to claim 1 including a computer coupled to the at least one sensor for recording and analyzing data recorded by the at least one sensor to thereby providing an indication of functioning of the system.

3. The testing system according to claim 1 including a fluid source in fluid communication with the wound cavity for delivering fluid to the wound cavity to simulate presence of exudates.

4. The testing system according to claim 1 wherein the exudates bath is adapted to supply at least one of exudates and fluid to the simulated wound.

5. The testing system according to claim 4 wherein the wound cavity of the simulated wound is configured and dimensioned to simulate at least one of the following types of wounds: a small dry wound, a small wet wound, a large dry wound, a large wet wound, and a tunneling wound, wherein the wet and dry characteristics arc controlled by fluid or exudates flow from the exudates bath.

6. The testing system according to claim 4 including a container in fluid communication with the negative pressure conduit and the negative pressure source to collect fluids or exudates removed from the wound cavity.

7. The testing system according to claim 6 wherein the container includes a fill sensor configured to detect a volume of fluids or exudates collected within the container.

8. The testing system according to claim 1 including a peristaltic pump operably associated with the exudates bath to maintain pressure therein and to provide desired pressure conditions for simulation purposes.

9. The testing system according to claim 1 wherein the housing of the simulated wound is constructed from at least one of the following materials: polycarbonate, metals, and plastics.

10. The testing system according to claim 1 wherein the wound cavity of the simulated wound is configured to remain rigid under pressure.

11. The testing system according to claim 1 wherein the wound cavity of the simulated wound is configured to collapse in order to simulate flexibility of human tissue in a clinical setting.

12. The testing system according to claim 1 wherein the negative pressure conduit includes a control valve for enabling a user to control the negative pressure source.

13. The testing system according to claim 1 including a plurality of negative pressure sources, each pressure source having individual control valves interchangeably connected to the negative pressure conduit to perform various tests and evaluate efficiency of the plurality of negative pressure sources.

14. The testing system according to claim 1 wherein the at least one sensor includes an oxygen sensor, a pressure sensor, a light sensor, a humidity sensor, a temperature sensor, and a bacterial level indicator.

15. The testing system according to claim 1 wherein the valve of the air leak model is controlled automatically through a valve control circuit to maintain a preset user selected flow rate.

16. The testing system according to claim 1 including a user interface configured to enable a user to monitor and adjust testing parameters.

* * * * *